(12) United States Patent
Bianchi et al.

(10) Patent No.: US 10,786,403 B2
(45) Date of Patent: *Sep. 29, 2020

(54) ABSORBENT ARTICLE WITH PROFILED ACQUISITION-DISTRIBUTION SYSTEM

(71) Applicant: The Procter & Gamble Company, Cincinnati, OH (US)

(72) Inventors: Ernesto Gabriel Bianchi, Oberursel (DE); Manuela Ines Schneider, Bensheim (DE); Gemma Baquer Molas, Schwalbach (DE); Nguyen Huynh-Trang Le, Bad Soden (DE)

(73) Assignee: The Procter & Gamble Company, Cincinnati, OH (US)

( * ) Notice: Subject to any disclaimer, the term of this patent is extended or adjusted under 35 U.S.C. 154(b) by 761 days.

This patent is subject to a terminal disclaimer.

(21) Appl. No.: 15/486,592

(22) Filed: Apr. 13, 2017

(65) Prior Publication Data

US 2017/0216109 A1    Aug. 3, 2017

Related U.S. Application Data

(60) Continuation of application No. 15/466,970, filed on Mar. 23, 2017, which is a division of application No.
(Continued)

(30) Foreign Application Priority Data

Dec. 10, 2012 (EP) ..................................... 12196348
Nov. 4, 2013 (EP) ..................................... 13191443

(51) Int. Cl.
*A61F 13/15*  (2006.01)
*A61F 13/537*  (2006.01)
(Continued)

(52) U.S. Cl.
CPC ........ *A61F 13/538* (2013.01); *A61F 13/1565* (2013.01); *A61F 13/15642* (2013.01);
(Continued)

(58) Field of Classification Search
CPC .... A61F 13/534; A61F 13/535; A61F 13/537; A61F 2013/53445; A61F 2013/53472;
(Continued)

(56) References Cited

U.S. PATENT DOCUMENTS 3,848,594 A  11/1974  Buell
3,860,003 A   1/1975  Buell
(Continued)

FOREIGN PATENT DOCUMENTS

DE    10204937 A1   8/2003
EP     0429112      5/1991
(Continued)

OTHER PUBLICATIONS

European Search Report, Appl. No. 12196348.2, dated Oct. 5, 2013, 5 pgs.

*Primary Examiner* — Kathryn E Ditmer
(74) *Attorney, Agent, or Firm* — Wednesday G. Shipp

(57) ABSTRACT

An absorbent article (20) having an absorbent core comprising at least about 80% of superabsorbent polymers (SAP) by weight of its absorbent material. An acquisition-distribution system (ADS) (50) is at least partially disposed between the absorbent core and the topsheet. The ADS extends in the longitudinal direction of the absorbent article at least from a point A1 disposed at a distance D from the front edge to a point A2 disposed at a distance D from the back edge of the article, D being equal to 32% of the length L of the article. The ADS has a basis weight which may be at least 20% lower at the point A2 than at the point A1.

8 Claims, 5 Drawing Sheets

Related U.S. Application Data

14/100,083, filed on Dec. 9, 2013, now Pat. No. 9,750,651.

(51) Int. Cl.
| | |
|---|---|
| *A61F 13/539* | (2006.01) |
| *A61F 13/53* | (2006.01) |
| *A61F 13/534* | (2006.01) |
| *A61F 13/538* | (2006.01) |
| *A61F 13/511* | (2006.01) |
| *A61F 13/512* | (2006.01) |

(52) U.S. Cl.
CPC ...... *A61F 13/512* (2013.01); *A61F 13/51113* (2013.01); *A61F 13/53* (2013.01); *A61F 13/534* (2013.01); *A61F 13/539* (2013.01); *A61F 13/53717* (2013.01); *A61F 2013/15349* (2013.01); *A61F 2013/5307* (2013.01); *A61F 2013/530051* (2013.01); *A61F 2013/5395* (2013.01); *A61F 2013/530481* (2013.01); *A61F 2013/530547* (2013.01); *A61F 2013/53908* (2013.01)

(58) Field of Classification Search
CPC ...... A61F 2013/5349; A61F 2013/5355; A61F 2013/53717; A61F 2013/53742; A61F 2013/53747

See application file for complete search history.

(56) References Cited

U.S. PATENT DOCUMENTS

| | | | |
|---|---|---|---|
| 3,911,173 A | 10/1975 | Sprague, Jr. | |
| 3,929,135 A | 12/1975 | Thompson | |
| 4,324,246 A | 4/1982 | Mullane et al. | |
| 4,340,706 A | 7/1982 | Obayashi et al. | |
| 4,342,314 A | 8/1982 | Radel et al. | |
| 4,463,045 A | 7/1984 | Ahr et al. | |
| 4,507,438 A | 3/1985 | Obayashi et al. | |
| 4,515,595 A | 5/1985 | Kievet et al. | |
| 4,573,986 A | 3/1986 | Minetola et al. | |
| 4,609,518 A | 9/1986 | Curro et al. | |
| 4,629,643 A | 12/1986 | Curro et al. | |
| 4,662,875 A | 5/1987 | Hirotsu et al. | |
| 4,666,983 A | 5/1987 | Tsubakimoto et al. | |
| 4,681,793 A | 7/1987 | Linman et al. | |
| 4,695,278 A | 9/1987 | Lawson | |
| 4,710,189 A | 12/1987 | Lash | |
| 4,731,066 A | 3/1988 | Korpman | |
| 4,785,996 A | 11/1988 | Ziecker et al. | |
| 4,795,454 A | 1/1989 | Dragoo | |
| 4,808,178 A | 2/1989 | Aziz | |
| 4,842,666 A | 6/1989 | Werenicz | |
| 4,846,815 A | 7/1989 | Scripps | |
| 4,894,060 A | 1/1990 | Nestegard | |
| 4,909,803 A | 3/1990 | Aziz et al. | |
| 4,946,527 A | 8/1990 | Battrell | |
| 4,963,140 A | 10/1990 | Robertson et al. | |
| 5,006,394 A | 4/1991 | Baird | |
| 5,137,537 A | 8/1992 | Herron et al. | |
| 5,147,345 A * | 9/1992 | Young | A61F 5/4401 |
| | | | 604/378 |
| 5,151,092 A | 9/1992 | Buell et al. | |
| 5,221,274 A | 6/1993 | Buell et al. | |
| 5,242,436 A | 9/1993 | Weil et al. | |
| 5,281,683 A | 1/1994 | Yano et al. | |
| 5,331,059 A | 7/1994 | Engelhardt et al. | |
| 5,409,771 A | 4/1995 | Dahmen et al. | |
| 5,433,715 A | 7/1995 | Tanzer et al. | |
| 5,462,537 A * | 10/1995 | Carr | A61F 13/45 |
| | | | 604/368 |
| 5,486,166 A | 1/1996 | Bishop et al. | |
| 5,490,846 A | 2/1996 | Ellis et al. | |
| 5,499,978 A | 3/1996 | Buell et al. | |
| 5,507,736 A | 4/1996 | Clear et al. | |
| 5,532,323 A | 7/1996 | Yano et al. | |
| 5,549,791 A | 8/1996 | Herron et al. | |
| 5,554,145 A | 9/1996 | Roe et al. | |
| 5,562,645 A | 10/1996 | Tanzer et al. | |
| 5,569,234 A | 10/1996 | Buell et al. | |
| 5,571,096 A | 11/1996 | Dobrin et al. | |
| 5,574,121 A | 11/1996 | Irie et al. | |
| 5,580,411 A | 12/1996 | Nease et al. | |
| 5,591,152 A | 1/1997 | Buell et al. | |
| 5,599,335 A | 2/1997 | Goldman et al. | |
| 5,607,414 A | 3/1997 | Richards et al. | |
| 5,607,760 A | 3/1997 | Roe et al. | |
| 5,609,587 A | 3/1997 | Roe | |
| 5,643,588 A | 7/1997 | Roe et al. | |
| 5,700,254 A | 12/1997 | McDowall et al. | |
| 5,837,789 A | 11/1998 | Stockhausen et al. | |
| 5,849,816 A | 12/1998 | Suskind et al. | |
| 5,865,823 A | 2/1999 | Curro | |
| 5,938,648 A | 8/1999 | Lavon et al. | |
| 5,968,025 A | 10/1999 | Roe et al. | |
| 6,004,306 A | 12/1999 | Roe et al. | |
| 6,121,509 A | 9/2000 | Ashraf et al. | |
| 6,143,821 A | 11/2000 | Houben | |
| 6,265,488 B1 | 7/2001 | Fujino et al. | |
| 6,414,216 B1 * | 7/2002 | Malowaniec | A61F 13/15203 |
| | | | 604/358 |
| 6,432,098 B1 | 8/2002 | Kline et al. | |
| 6,472,478 B1 | 10/2002 | Funk et al. | |
| 6,503,979 B1 | 1/2003 | Funk et al. | |
| 6,534,149 B1 | 3/2003 | Daley et al. | |
| 6,559,239 B1 | 5/2003 | Riegel et al. | |
| 6,632,504 B1 | 10/2003 | Gillespie et al. | |
| 6,645,569 B2 | 11/2003 | Cramer et al. | |
| 6,657,015 B1 | 12/2003 | Riegel et al. | |
| 6,716,441 B1 | 4/2004 | Roe et al. | |
| 6,863,933 B2 | 3/2005 | Cramer et al. | |
| 6,946,585 B2 | 9/2005 | Brown | |
| 7,112,621 B2 | 9/2006 | Rohrbaugh et al. | |
| 7,138,561 B2 | 11/2006 | Fuchs et al. | |
| 7,537,832 B2 | 5/2009 | Carlucci et al. | |
| 7,744,576 B2 | 6/2010 | Busam et al. | |
| 9,072,634 B2 | 7/2015 | Hundorf et al. | |
| 2002/0035353 A1 * | 3/2002 | Chmielewski | A61F 13/15658 |
| | | | 604/367 |
| 2002/0072471 A1 | 6/2002 | Ikeuchi et al. | |
| 2002/0123728 A1 | 9/2002 | Graef et al. | |
| 2002/0151634 A1 | 10/2002 | Rohrbaugh et al. | |
| 2002/0197695 A1 | 12/2002 | Glucksmann et al. | |
| 2003/0118764 A1 * | 6/2003 | Adams | A61F 13/535 |
| | | | 428/36.91 |
| 2003/0148684 A1 | 8/2003 | Cramer et al. | |
| 2003/0208175 A1 * | 11/2003 | Gross | A61F 13/53 |
| | | | 604/378 |
| 2004/0078016 A1 * | 4/2004 | Baker | A61F 13/15203 |
| | | | 604/378 |
| 2004/0162536 A1 | 8/2004 | Busam et al. | |
| 2004/0167486 A1 * | 8/2004 | Busam | A61F 13/539 |
| | | | 604/367 |
| 2005/0008839 A1 | 1/2005 | Cramer et al. | |
| 2005/0165208 A1 | 7/2005 | Popp et al. | |
| 2005/0176910 A1 | 8/2005 | Jaworek et al. | |
| 2005/0215752 A1 | 9/2005 | Popp et al. | |
| 2006/0024433 A1 | 2/2006 | Blessing et al. | |
| 2006/0155057 A1 | 7/2006 | Hermeling et al. | |
| 2006/0167215 A1 | 7/2006 | Hermeling et al. | |
| 2006/0211828 A1 | 9/2006 | Daniel et al. | |
| 2007/0043191 A1 | 2/2007 | Hermeling et al. | |
| 2007/0093767 A1 | 4/2007 | Carlucci et al. | |
| 2007/0118087 A1 | 5/2007 | Flohr et al. | |
| 2008/0021426 A1 * | 1/2008 | Nakagawa | A61F 13/534 |
| | | | 604/378 |
| 2008/0032035 A1 | 2/2008 | Schmidt et al. | |
| 2008/0091159 A1 | 4/2008 | Carlucci et al. | |
| 2008/0312617 A1 | 12/2008 | Hundorf et al. | |
| 2008/0312621 A1 | 12/2008 | Hundorf et al. | |
| 2008/0312622 A1 | 12/2008 | Hundorf et al. | |
| 2009/0192035 A1 | 7/2009 | Stueven et al. | |

(56) References Cited

U.S. PATENT DOCUMENTS

| | | |
|---|---|---|
| 2009/0258994 A1 | 10/2009 | Stueven et al. |
| 2009/0318884 A1 | 12/2009 | Meyer et al. |
| 2010/0051166 A1 | 3/2010 | Hundorf et al. |
| 2010/0068520 A1 | 3/2010 | Stueven et al. |
| 2010/0137823 A1* | 6/2010 | Corneliusson .... A61F 13/49012 604/365 |
| 2011/0250413 A1 | 10/2011 | Lu et al. |
| 2011/0268932 A1 | 11/2011 | Catalan et al. |
| 2011/0319848 A1 | 12/2011 | McKiernan et al. |
| 2012/0165776 A1 | 6/2012 | Rinnert et al. |
| 2014/0163504 A1 | 6/2014 | Bianchi et al. |

FOREIGN PATENT DOCUMENTS

| | | |
|---|---|---|
| EP | 530438 | 3/1993 |
| JP | 2010-75462 | 4/2010 |
| WO | WO 90/15830 | 12/1990 |
| WO | WO 93/21237 | 10/1993 |
| WO | WO 95/16746 | 6/1995 |
| WO | WO 95/24173 | 9/1995 |
| WO | WO 95/34329 | 12/1995 |
| WO | WO 99/17679 | 4/1999 |
| WO | WO 99/34841 | 7/1999 |
| WO | WO 2009/155265 | 12/2009 |
| WO | WO 2012/052172 | 4/2012 |

\* cited by examiner

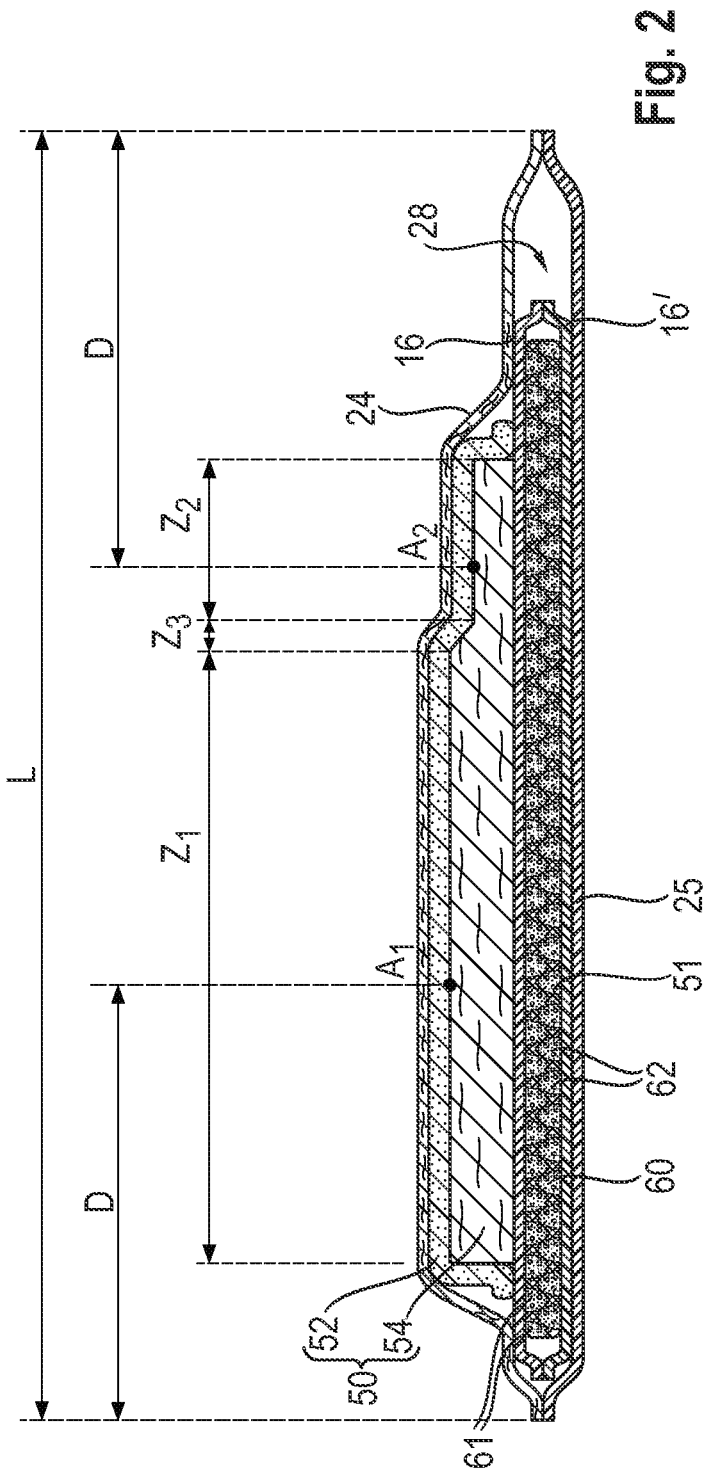
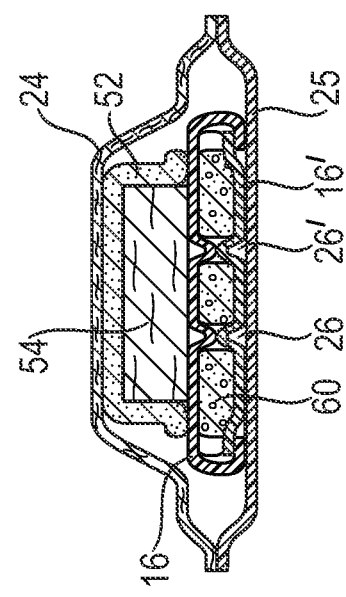

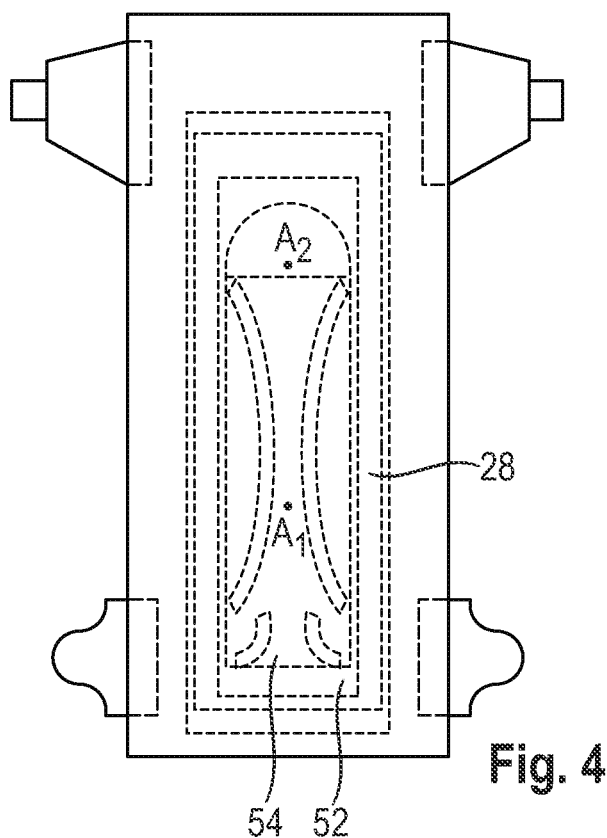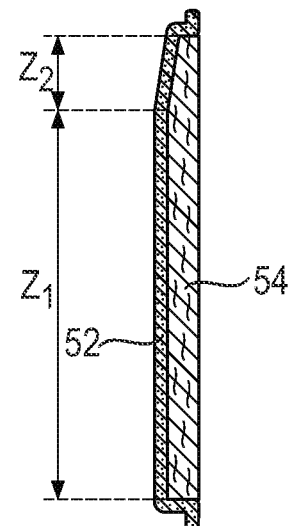
Fig. 4    Fig. 5
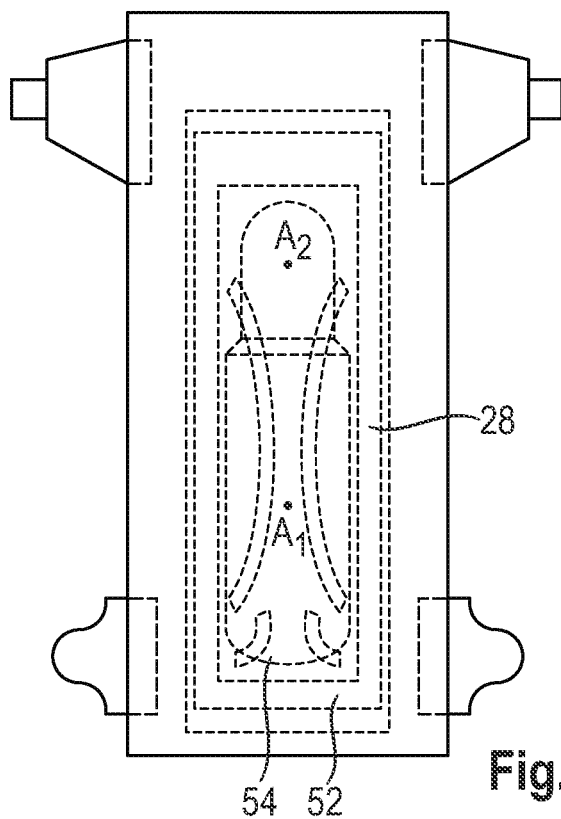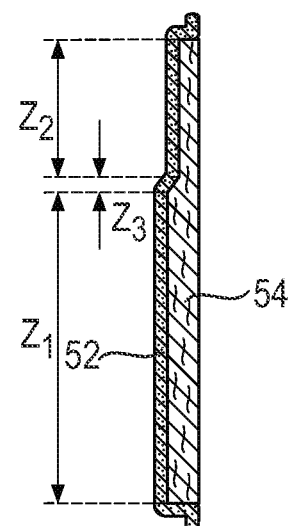
Fig. 6    Fig. 7

ABSORBENT ARTICLE WITH PROFILED ACQUISITION-DISTRIBUTION SYSTEM

FIELD OF THE INVENTION

The present invention is directed to absorbent articles, such as but not limited to baby diapers, feminine sanitary pads or training pants, comprising an acquisition-distribution system ("ADS") between the absorbent core and the topsheet. The ADS may comprise one, two or more layers and extends at least between two points (A1, A2) respectively disposed on the longitudinal axis of the article at a distance of 32% from the front edge and back edge of the absorbent article. The ADS has a higher basis weight at the point disposed further at the front of the article (A1) than at the point further at the back of the article (A2).

BACKGROUND OF THE INVENTION

Absorbent articles for personal hygiene, such as disposable diapers, feminine protection sanitary pads and adult incontinence undergarments, are designed to absorb and contain body exudates, in particular but not limited to urine. These absorbent articles usually comprise several layers having different functions, for example a topsheet, a backsheet and in-between an absorbent core, among other layers. The function of the absorbent core is to absorb and retain the exudates for a prolonged amount of time, for example overnight for a diaper, minimize re-wet to keep the wearer dry and avoid soiling of clothes or bed sheets.

The majority of currently marketed absorbent article comprise as absorbent material a blend of comminuted wood pulp with superabsorbent polymers (SAP) in particulate form, also called absorbent gelling materials (AGM), see for example U.S. Pat. No. 5,151,092 (Buell). Absorbent articles having a core consisting of essentially SAP as absorbent material (so called "airfelt-free" cores) have also been proposed but are less common than traditional mixed cores, see e.g. WO2008/155699 (Hundorf), WO95/11652 (Tanzer), WO2012/052172 (Van Malderen). Some absorbent cores have a profiled distribution of SAP towards the front of the absorbent core where more absorbent capacity is required because urine is typically delivered towards the front of the article.

It is known to provide a sub-layer, typically a non-woven, between the topsheet and the absorbent core. These sub-layers are designed to quickly acquire and/or distribute the fluid away from the topsheet and into the core. These sub-layers are sometimes called "wicking layer", "surge layer", "acquisition layer" or "distribution layer". Articles having only one of these sub-layers are known. Articles having two sub-layers or more, in particular a first sub-layer having a high capillarity which pulls the fluid quickly away from the topsheet and a second sub-layer a larger void area to distribute the fluid over a large surface over the core, are also known. These sub-layers typically do not comprise superabsorbent articles material. In the following, the term "acquisition-distribution system" ("ADS") will be used to designate the layer or combination of discrete layers (one, two, or more) present between the topsheet and the backsheet and providing these acquisition and/or distribution function, irrespective of the number of layers.

Acquisition-distribution systems comprising a single layer are disclosed for example in WO94/23761 (Payne), which discloses an acquisition layer comprising an homogeneous composition of hydrophilic fibrous material and a storage layer comprising a mixture of hydrophilic fibrous material and discrete particles of absorbent gelling material. The acquisition layer has an acquisition zone towards the front of the article of relatively lower average density and relatively lower average basis weight than a distribution zone towards the back of the article. Another example of ADS having a single layer can be found in U.S. Pat. Nos. 5,486,166 and 5,490,846 (Bishop).

US2008/0312621 and US2008/0312622 (Hundorf) describe a disposable absorbent article comprising a chassis including a topsheet and a backsheet, a substantially cellulose free absorbent core located between the topsheet and the backsheet and having a wearer facing side oriented toward a wearer when the article is being worn and an opposed garment facing side, and a "liquid acquisition system" comprising chemically cross-linked cellulosic fibers disposed between the liquid permeable topsheet and the wearer facing side of the absorbent core. The liquid acquisition system may also comprise an upper acquisition layer made of a latex bonded nonwoven.

WO99/17679 (Everett) discloses an absorbent core having multiple absorbent layers, wherein the absorbent layers interact in such a manner which preferentially locates absorbed liquid in an appointed, high saturation wicking layer within the core. This document also disclose a so-called "surge management layer" located on an inwardly facing body side surface of the topsheet layer. As shown in the drawings, this surge management layer is placed towards the front of the article and has a uniform basis weight along its length.

Typically absorbent cores have a higher absorbency capacity towards the front of the article as the fluid insult typically happens towards the front of the article. Acquisition-distribution systems have also been typically placed towards the front of the article for the same reason. After analyzing several hundred returned used diapers, the inventors have however surprisingly found that while it is true that the majority of the fluid insult happens towards the front of the article, a non negligible amount of fluid is also acquired in the article further back, in particular at a distance of approximately one third from the back edge of the article. The inventors surprisingly determined that the amount of fluid acquired in the back of the diaper can be as low as $\frac{1}{100}$ of the one acquired at the front, but sometimes as high as approximately half the amount acquired at the front in some special circumstances, such as high loads for baby girls laying on the back.

The inventors believe that at high loadings the fluid present towards the front of the article can saturate the absorbent material of the core, which slows its absorption. The inventors also believe that in some conditions, the fluid pooling between the skin and the topsheet can be lead by gravity towards the back of the absorbent article, especially if the wearer is sleeping on its back. This principle may be the cause of the surprising presence of high amount of fluid in the back of the diaper, which may cause of a non-negligible amount of diaper leakages during the night in the area of the back of the absorbent article. Although one solution to this problem would be to uniformly increase the basis weight of the existing acquisition-distribution system, this unfavorably increases production costs and may not prevent the fluid running at the surface of the wearer's skin.

The present inventors are proposing instead an improved construction for absorbent articles having absorbent cores with high concentration of SAP, which in particular may provide improvements in acquisition speed at high loading and/or during particular wearing conditions. The proposed ADS of the invention extends towards the back of the article at least to a certain point (A2) while at the same having a reduced basis weight towards the back of the article. The inventors have found that providing a reduced amount of acquisition-distribution material towards the back of the article at the point A2 was still sufficient to accommodate the lower amount of fluid expected in this part of the article.

In particular the inventors believe that the addition of a lower amount of acquisition-distribution material in the back of the article is sufficient to capture this lower amount of fluid reaching this area and improve the overall performance of the absorbent article. It is also believed that this new construction can improve the overall acquisition speed of the article without significantly increasing costs, even when the back of the core comprises relatively low amount of SAP. The inventors also believe that the acquisition-distribution material now placed towards the back of the article may be useful to acquire some of the fluid which first injured the article towards its front, and to later redistribute the fluid to the front of the core where the higher capacity is present. Additionally a lower basis weight for the acquisition distribution system at the back is believed to be beneficial to reduce the risk of saturating the back of the absorbent core, where capacity can be more limited than at the front.

SUMMARY OF THE INVENTION

The present invention is directed in a first aspect to absorbent articles as indicated in the claims. In particular the absorbent articles of the invention comprise a liquid permeable topsheet, a liquid impermeable backsheet, an absorbent core comprising at least 80% by weight of superabsorbent polymers, a core wrap enclosing the superabsorbent polymers and an acquisition distribution system (herein "ADS") at least partially disposed between the absorbent core and the topsheet. The ADS extends in the longitudinal direction of the absorbent article at least from a point A1 disposed at a distance D of the front edge to a point A2 disposed at a distance D from the back edge of the article, D being equal to 32% of the length L of the article. The ADS has a basis weight which is lower at the point A2 than at the point A1, in particular at least 20% lower.

The ADS may comprise one (i.e. a single) layer, two layers or more layers. The ADS may in particular comprise a distribution layer and an acquisition layer, the acquisition layer being at least partially disposed between the distribution layer and the topsheet. The absorbent article may further comprise channels substantially free of superabsorbent polymers and at least partially orientated in the longitudinal direction.

In a second aspect, the present invention is directed to a process for making absorbent articles according to the first aspect of the invention.

BRIEF DESCRIPTION OF THE DRAWINGS

FIG. 2 is a cross-section view of the absorbent article of FIG. 1 along its longitudinal axis 80;

FIG. 3 is a cross-section view of the absorbent article of FIG. 1 along its transversal axis 90;

FIGS. 4, 6, and 8 each show a top view of a different absorbent article according to the invention;

FIGS. 5, 7 and 9 show the respective longitudinal cross-section of the absorbent articles of FIGS. 4, 6 and 8.

DETAILED DESCRIPTION OF THE INVENTION

Definitions

Figure 1:
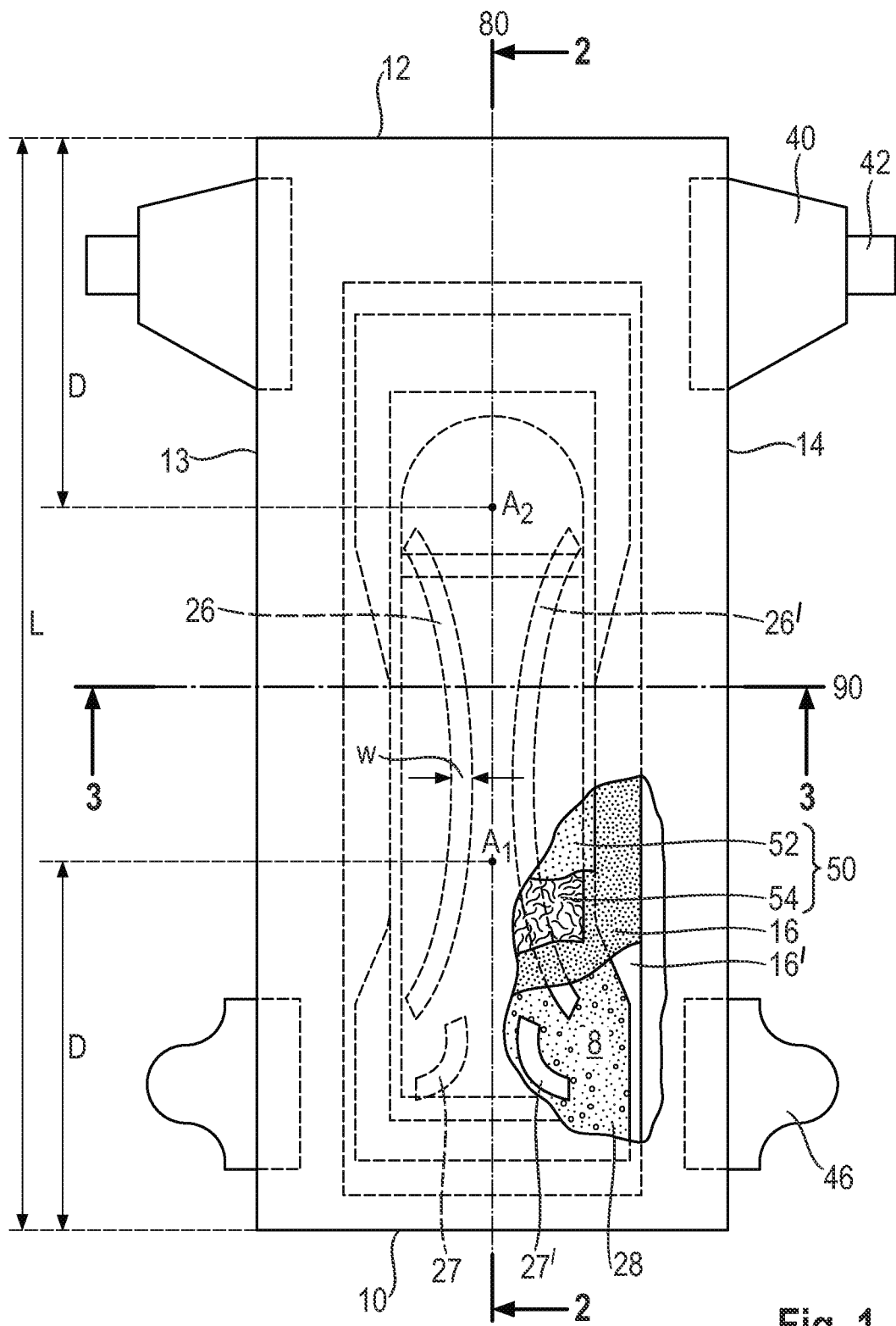
FIG. 1 is a top view of an absorbent article of the invention with some layers partially removed and comprising an ADS formed by combining an acquisition layer and a distribution layer.

As used herein, the term "absorbent article" refers to disposable devices such as infant or adult diapers, training pants, feminine hygiene articles and the like which are placed against or in proximity to the body of the wearer to absorb and contain the various exudates discharged from the body. Typically these articles comprise a topsheet, backsheet, an absorbent core, an acquisition-distribution system (which may be comprised of one or several layers) and possibly other components, with the absorbent core normally placed between the backsheet and the acquisition system or topsheet. The absorbent core is typically the component of the article having the most absorbent capacity. The absorbent articles of the invention will be further illustrated in the below description and in the Figures in the form of a taped diaper 20. Nothing in this description should be however considered limiting the scope of the claims unless explicitly indicated otherwise.

A "nonwoven web" as used herein means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yam). Nonwoven webs can be formed by many processes such as meltblowing, spunbonding, solvent spinning, electrospinning, carding and airlaying. The basis weight of nonwoven webs is usually expressed in grams per square meter (g/m$^2$).

"Comprise," "comprising," and "comprises" are open ended terms, each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essential of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "advantageously" and the likes also qualify features which are not intended to limit the scope of the claims unless specifically indicated to do so.

Unless indicated otherwise, the description refers to the absorbent article and its components before use (i.e. dry, and not loaded with a fluid) and conditioned at least 24 hours at 21° C.+/−2° C. and 50+/−20% Relative Humidity (RH).

General Description of the Absorbent Article Shown in the Figures

Figure 10:
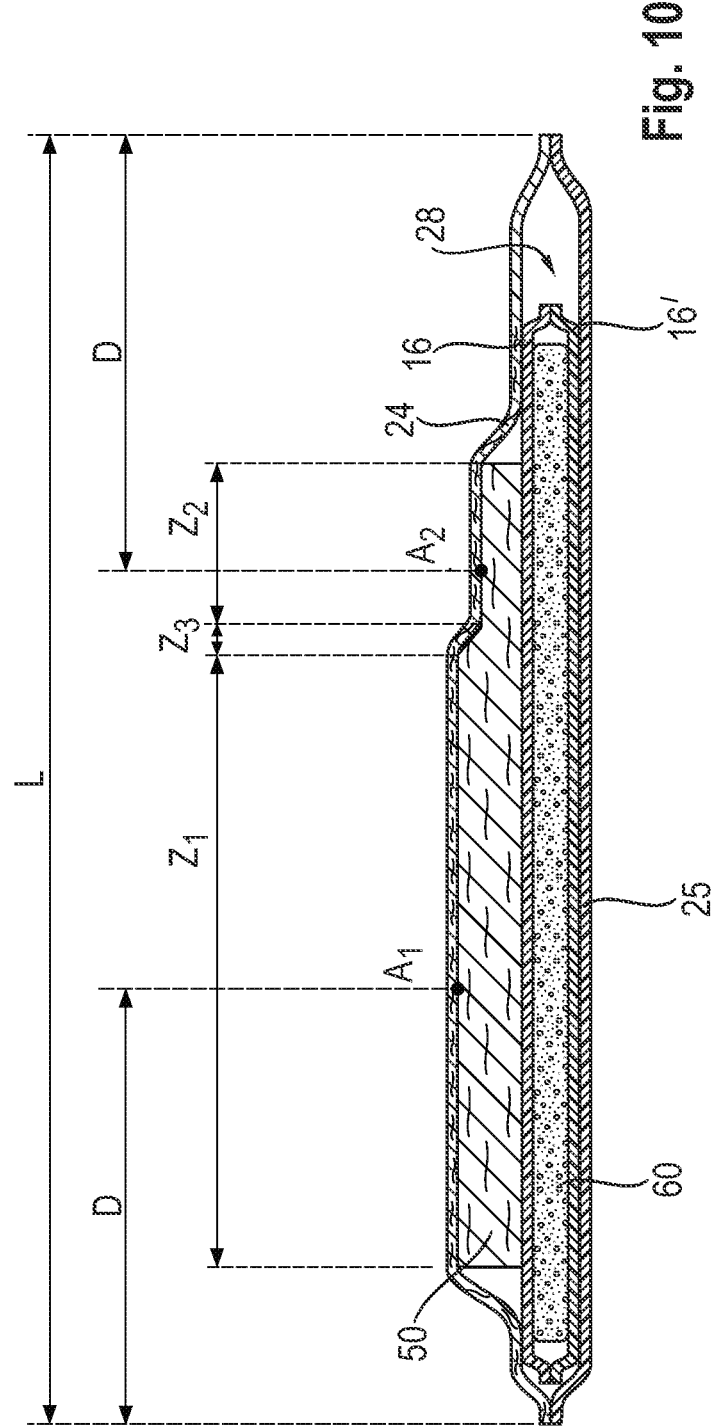
FIG. 10 shows a longitudinal cross-section view of an absorbent article of the invention having only one layer forming the ADS.

An exemplary absorbent article according to the invention in the form of an infant diaper 20 is represented in FIGS. 1-3. FIG. 1 is a plan view of the exemplary diaper 20, in a flat-out state, with portions of the structure being cut-away to more clearly show the construction of the diaper 20. This diaper 20 is shown for illustration purpose only as the invention may be used for making a wide variety of diapers or other absorbent articles. FIG. 10 shows for example a simpler diaper construction which is also part of the invention.

The absorbent article comprises a liquid permeable topsheet 24, a liquid impermeable backsheet 25, an absorbent core 28 disposed between the topsheet 24 and the backsheet 25. The absorbent articles also comprise an acquisition-distribution system 50 ("ADS"), which in the example represented comprises an acquisition layer 52 and a distribution layer 54, which will be further detailed in the following. FIG. 1 also shows typical diaper components such as a fastening system comprising adhesive tabs 42 cooperating with a landing zone on the front of the article (not represented). Other typical diaper components such as elasticized leg cuffs and barrier leg cuffs were not represented in the figures for clarity of depiction of the other components, but should be considered present as is common in taped diapers. The diaper may also comprise other typical elements, which are not represented, such as a back elastic waist feature, a front elastic waist feature, transverse barrier cuff(s), side panels, a lotion application, etc. . . . .

The absorbent article comprises a front edge 10, a back edge 12, and two side edges 13, 14. The front edge 10 is the edge of the article which is intended to be placed towards the front of the user when worn, and the back edge 12 is the opposite edge. The absorbent article when viewed from above in a flattened configuration as shown in FIG. 1 with topsheet up may be notionally divided by a longitudinal axis 80 extending from the front edge to the back edge of the article and dividing the article in two substantially symmetrical halves relative to this axis. The length L of the article can be measured along this longitudinal axis from the front edge to the back edge of the article. The absorbent article can be further notionally divided at half its length L (as measured on the longitudinal axis) by a transversal axis 90 perpendicular to the longitudinal axis in a front half and a back half. Typically in a diaper, the absorbent article is not substantially symmetrical along the transversal axis as the absorbent capacity is more concentrated towards the front of the diaper. The back half may typically comprise back ears 40 carrying the fastening tape 42, and the front half the landing zone (not represented) for the fastening tapes.

The topsheet 24, the backsheet 25, the absorbent core 28 and the other article components may be assembled in a variety of well known configurations, in particular by gluing or heat embossing. Exemplary diaper configurations are described generally in U.S. Pat. Nos. 3,860,003, 5,221,274, 5,554,145, 5,569,234, 5,580,411, and 6,004,306.

The absorbent articles of the invention comprise a profiled acquisition distribution system 50 extending in the longitudinal direction of the absorbent article at least from a point A1 disposed at a distance D of the front edge to a point A2 disposed at a distance D from the back edge of the article, D being equal to 32% of the length L of the article. The ADS has a basis weight which is at least 20% lower at the point A2 than at the point A1. Advantageously the ADS extends further than the points A1 and A2 towards the front and back edges of the article. However the ADS may advantageously not extend in the longitudinal and transversal direction beyond the absorbent material deposition area of the core to reduce the chance of leakage.

The absorbent core 28 comprises absorbent material comprising at least 80% by weight of superabsorbent polymers (herein "SAP") and a core wrap enclosing the absorbent material. The core wrap may typically comprise two substrates 16 and 16' for the top side and back side of the core. The core may further comprise channels 26, 26', which may be substantially free of superabsorbent polymers surrounded by the superabsorbent polymers, which may help the fluid to penetrate quicker within the core.

The absorbent article is preferably thin. The caliper at the front of the article as measured at the point A1 may be for example from 2.5 mm to 10.0 mm, in particular from 3.0 mm to 6.0 mm (see CALIPER measurement method below). The caliper at the back of the article as measured at the point A2 will be typically lower than at the point A1, as the basis weight, and hence the amount of material, of the ADS will be lower at the point A2. The caliper of the article at the point A2 may range in particular from 2.0 mm to 8.0 mm, in particular from 2.5 mm to 5.0 mm.

These and other components of the articles will now be discussed in more details.

Topsheet 24

The topsheet 24 is a part of the absorbent article that is directly in contact with the wearer's skin. The topsheet can be joined to the backsheet, the core and/or any other layers as is known in the art (as used herein, the term "joined" encompasses configurations whereby an element is directly secured to another element by affixing the element directly to the other element, and configurations whereby an element is indirectly secured to another element by affixing the element to intermediate member(s) which in turn are affixed to the other element). Usually, the topsheet 24 and the backsheet 25 are joined directly to each other in some locations (e.g. on or close to the periphery of the article) and are indirectly joined together in other locations by directly joining them to one or more other elements of the article 20.

The topsheet 24 is preferably compliant, soft-feeling, and non-irritating to the wearer's skin. Further, at least a portion of the topsheet 24 is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, meltblown, hydroentangled, or otherwise processed as is known in the art, in particular spunbond PP nonwoven. A suitable topsheet comprising a web of staple-length polypropylene fibers is manufactured by Veratec, Inc., a Division of International Paper Company, of Walpole, Mass. under the designation P-8.

Suitable formed film topsheets are also described in U.S. Pat. Nos. 3,929,135, 4,324,246, 4,342,314, 4,463,045, and 5,006,394. Other suitable topsheets 30 may be made in accordance with U.S. Pat. Nos. 4,609,518 and 4,629,643 issued to Curro et al. Such formed films are available from The Procter & Gamble Company of Cincinnati, Ohio as "DRI-WEAVE" and from Tredegar Corporation, based in Richmond, Va., as "CLIFF-T".

Any portion of the topsheet 24 may be coated with a lotion as is known in the art. Examples of suitable lotions include those described in U.S. Pat. Nos. 5,607,760, 5,609, 587, 5,643,588, 5,968,025 and 6,716,441. The topsheet 24 may also include or be treated with antibacterial agents, some examples of which are disclosed in PCT Publication WO95/24173. Further, the topsheet 24, the backsheet 25 or any portion of the topsheet or backsheet may be embossed and/or matte finished to provide a more cloth like appearance.

The topsheet 24 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 $cm^2$ and about 50 $cm^2$, in particular between about 15 $cm^2$ and 35 $cm^2$. Examples of apertured topsheet are disclosed in U.S. Pat. No. 6,632,504, assigned to BBA NONWOVENS SIMPSONVILLE. WO2011/163582 also discloses suitable colored topsheet having a basis weight of from 12 to 18 gsm and comprising a plurality of bonded points. Each of the bonded points has a surface area of from 2 $mm^2$ to 5 $mm^2$ and the cumulated surface area of the plurality of bonded points is from 10 to 25% of the total surface area of the topsheet.

Typical diaper topsheets have a basis weight of from about 10 to about 28 gsm, in particular between from about 12 to about 18 gsm but other basis weights are possible.

Backsheet 25

The backsheet 25 is generally that portion of the article 20 positioned adjacent the garment-facing surface of the absorbent core 28 and which prevents the exudates absorbed and contained therein from soiling articles such as bedsheets and undergarments. The backsheet 25 is typically impermeable to liquids (e.g. urine). The backsheet may for example be or comprise a thin plastic film such as a thermoplastic film having a thickness of about 0.012 mm to about 0.051 mm. Exemplary backsheet films include those manufactured by Tredegar Corporation, based in Richmond, Va., and sold under the trade name CPC2 film. Other suitable backsheet materials may include breathable materials which permit vapors to escape from the diaper 20 while still preventing exudates from passing through the backsheet 25. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 to LaVon et al., U.S. Pat. No. 4,681,793 to Linman et al., U.S. Pat. No. 5,865,823 to Curro; and U.S. Pat. No. 5,571,096 to Dobrin et al, U.S. Pat. No. 6,946,585B2 to London Brown.

The backsheet 25 may be joined to the topsheet 24, the absorbent core 28 or any other element of the diaper 20 by any attachment means known in the art. Suitable attachment means are described above with respect to means for joining the topsheet 24 to other elements of the article 20. For example, the attachment means may include a uniform continuous layer of adhesive, a patterned layer of adhesive, or an array of separate lines, spirals, or spots of adhesive. Suitable attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. Nos. 3,911,173, 4,785,996; and 4,842,666. Adhesives which have been found to be satisfactory are manufactured by H. B. Fuller Company of St. Paul, Minn. and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

Absorbent Core 28

As used herein, the term "absorbent core" refers to an independent component suitable for use in an absorbent article comprising absorbent material with a high amount of superabsorbent polymers (herein abbreviated as "SAP") enclosed within a core wrap. The superabsorbent polymers content in the core is relatively high and represents at least 80% by weight of the absorbent material contained in the core wrap. By "absorbent material" it is meant all the materials which have some absorbency property or liquid retaining properties such as SAP, cellulosic fibers as well as synthetic fibers. Typically, glues used in making absorbent cores have no absorbency properties and are not considered as absorbent material. The SAP content may be higher, for example at least 85%, at least 90%, at least 95% and even up to and including 100% of the weight of the absorbent material contained within the core wrap. This provides a relatively thin core compared to conventional core comprising between 40-60% SAP and high content of cellulose fibers. The absorbent material may in particular comprises less than 10% weight percent of natural or synthetic fibers, or less than 5% weight percent, or even be substantially free of natural and/or synthetic fibers. The absorbent material may advantageously comprise little or no airfelt (cellulose) fibers, in particular the absorbent core may comprise less than 15%, 10%, 5% airfelt (cellulose) fibers by weight of the absorbent core, or even be substantially free of cellulose fibers.

The absorbent core of the invention may further comprise adhesive for example to help immobilizing the SAP within the core wrap and/or to ensure integrity of the core wrap, in particular when the core wrap is made of two or more substrates. The core wrap will typically extend to a larger area than strictly needed for containing the absorbent material within. The absorbent material within the core wrap comprising at least 80% SAP forms an area within the core wrap which will be referred to as Absorbent material deposition area in the following.

Examples of cores comprising relatively high amount of SAP are known, and various core design have been proposed in the past, for example in U.S. Pat. No. 5,599,335 (Goldman), EP1,447,066 (Busam), WO95/11652 (Tanzer) or US2008/0312622A1 (Hundorf), WO2012/052172 (Van Malderen). In some embodiments, these cores comprise a layer of SAP comprised of individual pockets or stripes of SAP enclosed within the core wrap. In other embodiments, the cores comprise a continuous layer of SAP enclosed within the core wrap. The continuous layer of SAP may be in particular be obtained by combining two absorbent layers having discontinuous SAP application pattern wherein the resulting layer of SAP is substantially continuously distributed across the absorbent particulate polymer material area.

As illustrated in a particular example in FIG. 2, the absorbent core may comprise a first absorbent layer and a second absorbent layer, the first absorbent layer comprising a first substrate 16 and a first layer of SAP 61, the second absorbent layer comprising a second substrate 16' and a second layer of SAP 62, and a fibrous thermoplastic adhesive material 51 at least partially bonding the layers of SAP to their respective substrate, the first substrate and the second substrate forming the core wrap. By "SAP" it is meant an absorbent material comprising at least 80% SAP and advantageously up to 100%. The SAP layers may be deposited on their respective substrate in a deposition pattern comprising land areas comprising SAP particles and junction areas between the land areas being free of SAP. In the example of FIG. 2 these land areas are longitudinally extending across the width of absorbent material deposition area 8. The fibrous thermoplastic adhesive material is then at least partially in contact with the SAP in the land areas and at least partially in contact with the substrate layer in the junction areas. This imparts an essentially three-dimensional structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the SAP in the land area, and thereby immobilizes this material.

The thermoplastic adhesive material may comprise, in its entirety, a single thermoplastic polymer or a blend of thermoplastic polymers, having a softening point, as determined by the ASTM Method D-36-95 "Ring and Ball", in the range between 50° C. and 300° C., and/or the thermoplastic adhesive material may be a hotmelt adhesive comprising at least one thermoplastic polymer in combination with other thermoplastic diluents such as tackifying resins, plasticizers and additives such as antioxidants.

The thermoplastic polymer has typically a molecular weight (Mw) of more than 10,000 and a glass transition temperature (Tg) usually below room temperature or $-6°$ C.$<$Tg$<16°$ C. Typical concentrations of the polymer in a hotmelt are in the range of about 20 to about 40% by weight. The thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

The tackifying resin may exemplarily have a Mw below 5,000 and a Tg usually above room temperature, typical concentrations of the resin in a hotmelt are in the range of about 30 to about 60%, and the plasticizer has a low Mw of typically less than 1,000 and a Tg below room temperature, with a typical concentration of about 0 to about 15%.

The adhesive used for the fibrous layer preferably has elastomeric properties, such that the web formed by the fibers on the SAP is able to be stretched as SAP swell. Exemplary elastomeric, hotmelt adhesives include thermoplastic elastomers such as ethylene vinyl acetates, polyurethanes, polyolefin blends of a hard component (generally a crystalline polyolefin such as polypropylene or polyethylene) and a Soft component (such as ethylene-propylene rubber); copolyesters such as poly (ethylene terephthalate-co-ethylene azelate); and thermoplastic elastomeric block copolymers having thermoplastic end blocks and rubbery mid blocks designated as A-B-A block copolymers: mixtures of structurally different homopolymers or copolymers, e.g., a mixture of polyethylene or polystyrene with an A-B-A block copolymer; mixtures of a thermoplastic elastomer and a low molecular weight resin modifier, e.g., a mixture of a styrene-isoprenestyrene block copolymer with polystyrene; and the elastomeric, hot-melt, pressure-sensitive adhesives described herein. Elastomeric, hot-melt adhesives of these types are described in more detail in U.S. Pat. No. 4,731,066 issued to Korpman on Mar. 15, 1988.

The thermoplastic adhesive material is applied as fibers. The fibers may exemplarily have an average thickness of about 1 to about 50 micrometers or about 1 to about 35 micrometers and an average length of about 5 mm to about 50 mm or about 5 mm to about 30 mm. To improve the adhesion of the thermoplastic adhesive material to the substrate or to any other layer, in particular any other nonwoven layer, such layers may be pre-treated with an auxiliary adhesive. The fibers adhere to each other to form a fibrous layer, which can also be described as a mesh.

In certain embodiments, the thermoplastic adhesive material will meet at least one, or several, or all of the following parameters. An exemplary thermoplastic adhesive material may have a storage modulus G' measured at 20° C. of at least 30,000 Pa and less than 300,000 Pa, or less than 200,000 Pa, or between 140,000 Pa and 200,000 Pa, or less than 100,000 Pa. In a further aspect, the storage modulus G' measured at 35° C. may be greater than 80,000 Pa. In a further aspect, the storage modulus G' measured at 60° C. may be less than 300,000 Pa and more than 18,000 Pa, or more than 24,000 Pa, or more than 30,000 Pa, or more than 90,000 Pa. In a further aspect, the storage modulus G' measured at 90° C. may be less than 200,000 Pa and more than 10,000 Pa, or more than 20,000 Pa, or more then 30,000 Pa. The storage modulus measured at 60° C. and 90° C. may be a measure for the form stability of the thermoplastic adhesive material at elevated ambient temperatures. This value is particularly important if the absorbent product is used in a hot climate where the thermoplastic adhesive material would lose its integrity if the storage modulus G' at 60° C. and 90° C. is not sufficiently high.

G' can be measured using a rheometer as indicated in WO2010/27719. The rheometer is capable of applying a shear stress to the adhesive and measuring the resulting strain (shear deformation) response at constant temperature. The adhesive is placed between a Peltier-element acting as lower, fixed plate and an upper plate with a radius R of e.g., 10 mm, which is connected to the drive shaft of a motor to generate the shear stress. The gap between both plates has a height H of e.g., 1500 micron. The Peltier-element enables temperature control of the material (+0.5° C.). The strain rate and frequency should be chosen such that all measurements are made in the linear viscoelastic region.

The absorbent core advantageously achieve an SAP loss of no more than about 70%, 60%, 50%, 40%, 30%, 20%, 10% according to the Wet Immobilization Test described in WO2010/0051166A1.

Superabsorbent Polymer (SAP)

"Superabsorbent polymers" as used herein refer to absorbent material which are cross-linked polymeric materials that can absorb at least 10 times their weight of an aqueous 0.9% saline solution as measured using the Centrifuge Retention Capacity (CRC) test (EDANA method WSP 241.2-05E). The SAP of the invention may in particular have a CRC value of more than 20 g/g, or more than 24 g/g, or of from 20 to 50 g/g, or from 20 to 40 g/g, or 24 to 30 g/g. The SAP useful in the present invention include a variety of water-insoluble, but water-swellable polymers capable of absorbing large quantities of fluids.

The SAP can be in particulate form so as to be flowable in the dry state. Typical particulate absorbent polymer materials are made of poly(meth)acrylic acid polymers. However, e.g. starch-based particulate absorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked. Suitable materials are described in the PCT Patent Application WO07/047598 or for example WO07/046052 or for example WO2009/155265 and WO2009/155264. In some embodiments, suitable SAP particles may be obtained by current state of the art production processes as is more particularly as described in WO 2006/083584. The SAP are preferably internally cross-linked, i.e. the polymerization is carried out in the presence of compounds having two or more polymerizable groups which can be free-radically copolymerized into the polymer network. Useful crosslinkers include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in DE-A 103 31 450, mixed acrylates which, as well as acrylate groups, include further ethylenically unsaturated groups, as described in DE-A 103 31 456 and DE-A 103 55 401, or crosslinker mixtures as described for example in DE-A 195 43 368, DE-A 196 46 484, WO90/15830 and WO02/32962 as well as cross-linkers described in WO2009/155265. The superabsorbent polymer particles may be externally surface cross-linked, or: post cross-linked). Useful post-crosslinkers include compounds including two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019, cyclic carbonates as described in DE-A 40 20 780, 2-oxazolidone and its derivatives, such as N-(2-hydroxyethyl)-2-oxazolidone as described in DE-A 198 07 502, bis- and poly-2-oxazolidones as described in DE-A 198 07 992, 2-oxotetrahydro-1,3-oxazine and its derivatives as described in DE-A 198 54 573, N-acyl-2-oxazolidones as described in DE-A 198 54 574, cyclic ureas as described in DE-A102 04 937, bicyclic amide acetals as described in DE-A 103 34 584, oxetane and cyclic ureas as described in EP-A 1 199 327 and morpholine-2,3-dione and its derivatives as described in WO 03/031482.

In some embodiments, the SAP are formed from polyacrylic acid polymers/polyacrylate polymers, for example having a neutralization degree of from 60% to 90%, or about 75%, having for example sodium counter ions.

The SAP useful for the present invention may be of numerous shapes. The term "particles" refers to granules, fibers, flakes, spheres, powders, platelets and other shapes and forms known to persons skilled in the art of superabsorbent polymer particles. In some embodiments, the superabsorbent polymer particles can be in the shape of fibers, i.e. elongated, acicular superabsorbent polymer particles. In those embodiments, the superabsorbent polymer particles fibers have a minor dimension (i.e. diameter of the fiber) of less than about 1 mm, usually less than about 500 µm, and preferably less than 250 µm down to 50 µm. The length of the fibers is preferably about 3 mm to about 100 mm. The fibers can also be in the form of a long filament that can be woven.

Typically, SAP are spherical-like particles. In contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 or from 50 to 850 preferably from 100 to 500 more preferably from 150 to 300 as measured according to EDANA method WSP 220.2-05. SAP having a relatively low particle size help to increase the surface area of the absorbent material which is in contact with liquid exudates and therefore support fast absorption of liquid exudates.

The SAP may have a particle sizes in the range from 45 µm to 4000 µm, more specifically a particle size distribution within the range of from 45 µm to about 2000 µm, or from about 100 µm to about 1000, 850 or 600 µm. The particle size distribution of a material in particulate form can be determined as it is known in the art, for example by means of dry sieve analysis (EDANA 420.02 "Particle Size distribution).

In some embodiments herein, the superabsorbent material is in the form of particles with a mass medium particle size up to 2 mm, or between 50 microns and 2 mm or to 1 mm, or preferably from 100 or 200 or 300 or 400 or 500 µm, or to 1000 or to 800 or to 700 µm; as can for example be measured by the method set out in for example EP-A-0691133. In some embodiments of the invention, the superabsorbent polymer material is in the form of particles whereof at least 80% by weight are particles of a size between 50 µm and 1200 µm and having a mass median particle size between any of the range combinations above. In addition, or in another embodiment of the invention, said particles are essentially spherical. In yet another or additional embodiment of the invention the superabsorbent polymer material has a relatively narrow range of particle sizes, e.g. with the majority (e.g. at least 80% or preferably at least 90% or even at least 95% by weight) of particles having a particle size between 50 µm and 1000 µm, preferably between 100 µm and 800 µm, and more preferably between 200 µm and 600 µm.

Suitable SAP may for example be obtained from inverse phase suspension polymerizations as described in U.S. Pat. Nos. 4,340,706 and 5,849,816 or from spray- or other gas-phase dispersion polymerizations as described in US Patent Applications No. 2009/0192035, 2009/0258994 and 2010/0068520. In some embodiments, suitable SAP may be obtained by current state of the art production processes as is more particularly described from page 12, line 23 to page 20, line 27 of WO 2006/083584.

The surface of the SAP may be coated, for example, with a cationic polymer. Preferred cationic polymers can include polyamine or polyimine materials. In some embodiments, the SAP may be coated with chitosan materials such as those disclosed in U.S. Pat. No. 7,537,832 B2. In some other embodiments, the SAP may comprise mixed-bed Ion-Exchange absorbent polymers such as those disclosed in WO 99/34841 and WO 99/34842.

The absorbent core will typically comprise only one type of SAP, but it is not excluded that a blend of SAPs may be used. The fluid permeability of a superabsorbent polymer can be quantified using its Urine Permeability Measurement (UPM) value, as measured in the test disclosed European patent application number EP12174117.7. The UPM of the SAP may for example be of at least $10 \times 10^{-7}$ cm$^3$·sec/g, or at least $30 \times 10^{-7}$ cm$^3$·sec/g, or at least $50 \times 10^{-7}$ cm$^3$·sec/g, or more, e.g. at least 80 or $100 \times 10^{-7}$ cm$^3$·sec/g. The flow characteristics can also be adjusted by varying the quantity and distribution of the SAP used in the second absorbent layer.

For most absorbent articles, the liquid discharge occurs predominately in the front half of the article, in particular for diaper. The front half of the article (as defined by the transversal centerline 90) may therefore comprise most of the absorbent capacity of the core. Thus, at least 60% of the SAP, or at least 65%, 70%, 75% or 80% of the SAP may be present in the front half of the absorbent article, the remaining SAP being disposed in the back half of the absorbent article.

The total amount of SAP present in the absorbent core may also vary according to expected user. Feminine protection articles or diapers for new born may require much less SAP than infant or adult incontinence diapers. For infant diapers the total amount of SAP may be for example comprised from about 1 to 50 g, in particular from 2 to 20 g. The average basis weight of the SAP within the (or "at least one", if several are present) absorbent material deposition area may be of at least 50, 100, 200, 300, 400, 500 or more g/m$^2$.

Core Wrap (16, 16')

The core wrap may be made of one substrate folded around the absorbent material of the core, or may comprise two or more substrates which are attached to another, for example in a so-called sandwich wrap, or a so called C-wrap as shown in FIGS. 2 and 3, where the longitudinal (and/or transversal) edges of one of the substrate are folded over the other substrate.

The core wrap may be formed by any materials suitable for receiving the absorbent materials deposited thereon. Typical substrate materials used in the production of conventional cores may be used, in particular paper, tissues, films, wovens or nonwovens, or laminate of any of these. The first and second substrates may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US2011/0268932A1, US2011/0319848A1 or US2011/0250413A1. Nonwoven materials provided from synthetic fibers may be used, such as PE, PET and in particular PP.

If the core wrap comprises a first substrate 16 and a second substrate 16' these may be made of the same type of material, or may be made of different materials or one of the substrate may be treated differently than the other to provide it with different properties. As the polymers used for nonwoven production are inherently hydrophobic, they are preferably coated with hydrophilic coatings if placed on the fluid receiving side of the absorbent core. A possible way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven. An alternative possible way to produce nonwovens with durably hydrophilic coatings is to coat the nonwoven with hydrophilic nanoparticles, e.g. as described in WO 02/064877.

Permanently hydrophilic nonwovens are also useful in some embodiments. Surface tension, as described in U.S. Pat. No. 7,744,576 (Busam et al.), can be used to measure how permanently a certain hydrophilicity level is achieved. Liquid strike through, as described in U.S. Pat. No. 7,744,576, can be used to measure the hydrophilicity level. The first and/or second substrate may in particular have a surface tension of at least 55, preferably at least 60 and most preferably at least 65 mN/m or higher when wetted with saline solution. The substrate may also have a liquid strike through time of less than 5 s for a fifth gush of liquid. These values can be measured using the test methods described in U.S. Pat. No. 7,744,576B2: "Determination Of Surface Tension" and "Determination of Strike Through" respectively.

Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A substrate having a lower contact angle between the water and the surface of substrate may be said to be more hydrophilic than another.

The substrates may also be air-permeable. Films useful herein may therefore comprise micro-pores. The first and second substrate may have for example an air-permeability of from 40 or from 50, to 300 or to 200 m$^3$/(m$^2$×min), as determined by EDANA method 140-1-99 (125 Pa, 38.3 cm$^2$). The first and/or second substrate may alternatively have a lower air-permeability, e.g. being non-air-permeable, for example to facilitate handling on a moving surface comprising vacuum.

As shown in FIG. 3 for example, the first substrate 16 may be placed on one side of the core (the top side as represented therein) and extends around the core's longitudinal edges to partially wrap the opposed (bottom) side of the core. The second substrate 16' can be positioned between the wrapped flaps of the first substrate 16 and the rest of the core. The flaps of the first substrate 16 and the second substrate 16' may be glued. This so called C-wrap construction can provide benefits such as improved resistance to bursting in a wet loaded state. The transversal edges of the core may then also be sealed for example by gluing to provide complete encapsulation of the absorbent materials of the core across the whole of the periphery of the core. As an alternate construction, in the so-called sandwich construction, the first and second substrates may extend outwardly and be sealed along the whole or parts of the periphery of the core, for example along the longitudinal edges of the core, typically by gluing and/or heat/pressure bonding.

Typically neither first nor second substrates need to be shaped, so that they can be rectangularly cut for ease of production but of course other shapes are possible.

Absorbent Material Deposition Area 8

Figure 8:
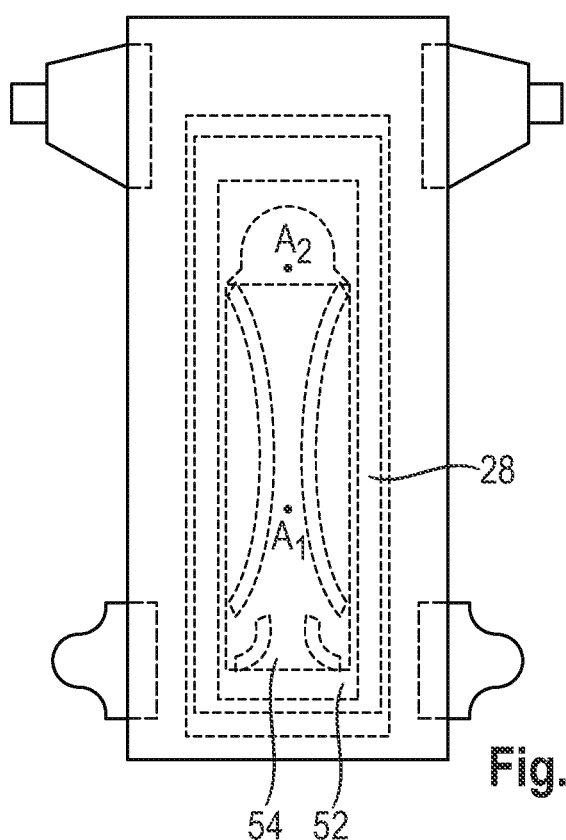
Figure 9:
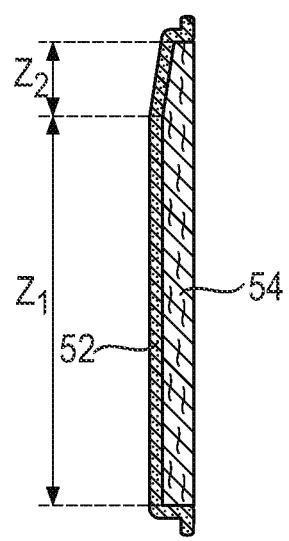

The deposition area 8 of the absorbent material can be defined by the periphery of the layer formed by the absorbent material within the core wrap as viewed from the top of the flattened article, as shown in FIG. 1. The absorbent material deposition area 8 can take various shapes, in particular display a so-called "dog bone" or "hour-glass" shape, which shows a tapering along its width in the middle or "crotch" region of the core, as exemplarily shown in the embodiment of FIG. 1. In this way, the absorbent material deposition area may have a relatively narrow width in an area of the core intended to be placed in the crotch region of the absorbent article. This may provide for example better wearing comfort. The absorbent material deposition area 8 may thus have a width (as measured in the transversal direction) at its narrowest point which is less than about 100 mm, 90 mm, 80 mm, 70 mm, 60 mm or even less than about 50 mm. This narrowest width may further be for example at least 5 mm, or at least 10 mm, smaller than the width of the deposition area at its largest point in the front and/or back regions of the deposition area 8. The absorbent material deposition area 8 can also be generally rectangular, for example as shown in FIGS. 6 and 8, but other deposition areas can also be used such as a "T" or "Y" shape".

The basis weight (amount deposited per unit of surface) of the SAP may also be varied along the deposition area 8 to create a profiled distribution of the SAP in the longitudinal direction, in the transversal direction, or both directions of the core. Hence along the longitudinal axis of the core, the basis weight of the SAP deposited in different land areas may be varied, as well as along the transversal axis, or any axis parallel to any of these axis. When the SAP deposition pattern comprises land areas separated by junction areas, the basis weight of SAP in a land area of relatively high basis weight may thus be for example at least 10%, or 20%, or 30%, or 40%, or 50% higher than in a land area of relatively low basis weight. In particular the land areas present in a deposition area of the core having a narrowed width, or more generally a small surface area, (for example in a middle or intermediate region between the front and back regions of the core) may have on average more SAP per unit of surface deposited as compared to other deposition areas having a larger deposition area.

The SAP layer may be deposited using known techniques which allow relatively precise deposition of SAP at relatively high speed. In particular the SAP printing technology as disclosed for example in US2006/24433 (Blessing), US2008/0312617 and US2010/0051166A1 (both to Hundorf et al.) may be used. This technique uses a printing roll to deposit SAP onto a substrate disposed on a grid of a support which may include a plurality of cross bars extending substantially parallel to and spaced from one another so as to form channels extending between the plurality of cross-bars. This technology allows high-speed and precise deposition of SAP on a substrate.

Acquisition-Distribution System ("ADS")

The absorbent articles of the invention comprise an acquisition-distribution system (referred to herein as "ADS") between the topsheet and the absorbent core. The function of the ADS is to acquire the fluid and/or distribute it to the absorbent core in an efficient manner. The ADS may comprise one, two or more layers. When the ADS comprises two or more layers, these may be bonded together but remain discrete layers that can be clearly identified. The ADS may also be formed by a single layer which may be a homogeneous layer or be formed by two or more sub-layers with different properties that are closely integrated together, for example by fiber intermeshing, so that the ADS can be handled as a single discrete layer.

In the examples represented in the FIG. 1-9, the ADS comprises two discrete layers: a distribution layer 54 and an acquisition layer 52 disposed between the absorbent core and the topsheet. In the example represented in FIG. 10, the ADS comprises a single layer or material 60, which may be a material according to the distribution layer or acquisition layer further detailed below, or any of the other materials commercially available or known in the art for example as indicated in WO94/23761 (Payne), WO2000/59430 (Daley), WO95/10996 (Richards), U.S. Pat. No. 5,700,254 (McDowall), WO02/067809 (Graef), U.S. Pat. Nos. 5,486,166 and 5,490,846 (Bishop). The prior art discloses many types of acquisition-distribution systems comprising a single layer.

According to the invention, the ADS extends along the longitudinal axis of the article at least between the points A1 and A2. These points are disposed on the longitudinal axis and spaced respectively from the front edge and back edge of the article by a distance D, with D equal to 32% of the length L of the article along the longitudinal axis. The ADS may be advantageously disposed at least 5 mm, or 10 mm, or 15 mm further beyond these points towards the front and/or back edges of the absorbent article. If the ADS comprises more than one layer, these may be of different lengths and/or width, but advantageously all the layers will extend at least between A1 and A2.

According to the invention, the ADS has a basis weight which is lower at the point A2 disposed further to the back of the article than at the point A1. The basis weight of the ADS may be in particular at least 20% lower at A2 than at A1. This basis weight difference between the ADS at the point A1 and the point A2 may be for example from 20% to 90%, or 30% to 70%. If the ADS comprises more than one layer, the basis weight difference between the points A1 and A2 may be provided by a weight difference in one or more of the layers of the ADS. In the non-limiting example as shown in the FIGS. 1-9, the basis weight difference is due to a difference in the basis weight of the distribution layer, the acquisition layer remaining at equal basis weight along its length, as will further detailed below.

The ADS or any components thereof may also be profiled in the transversal (CD) direction. For example the basis weight of the ADS or any of its components may be higher along the longitudinal axis of the article compared to the lateral sides thereof. This can be achieved by having a component of the ADS larger than the other component in the transversal direction (for example as represented in the Figures, the acquisition layer 52 is larger than the distribution layer 54) of profiling in cross-direction one layer of ADS, for example the distribution layer exemplified in this description comprising cross-linked cellulose.

Typically, the ADS will not comprise SAP as this may slow the acquisition and distribution of the fluid. The ADS may comprise, although not necessarily, two layers: a distribution layer and an acquisition layer, which will now be discussed in more details.

Distribution Layer 54

The function of a distribution layer 54 is to spread the insulting fluid liquid over a larger surface within the article so that the absorbent capacity of the core can be more efficiently used. Typically distribution layer are made of a nonwoven material based on synthetic or cellulosic fibers and having a relatively low density. The density of the distribution layer may vary depending on the compression of the article, but may typically range from 0.03 to 0.25 g/cm$^3$, in particular from 0.05 to 0.15 g/cm$^3$ measured at 0.30 psi (2.07 kPa). The distribution layer 54 may also be a material having a water retention value of from 25 to 60, preferably from 30 to 45, measured as indicated in the procedure disclosed in U.S. Pat. No. 5,137,537.

The distribution layer may for example comprise at least 50% by weight of cross-linked cellulose fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf) however not in the profiled manner of the invention. The cross-linked cellulosic fibers provide higher resilience and therefore higher resistance to the first absorbent layer against the compression in the product packaging or in use conditions, e.g. under baby weight. This provides the core with a higher void volume, permeability and liquid absorption, and hence reduced leakage and improved dryness.

Exemplary chemically cross-linked cellulosic fibers suitable for a distribution layer are disclosed in U.S. Pat. Nos. 5,549,791, 5,137,537, WO9534329 or US2007/118087. Exemplary cross-linking agents include polycarboxylic acids such as citric acid and/or polyacrylic acids such as acrylic acid and maleic acid copolymers. For example, the crosslinked cellulosic fibers may have between about 0.5 mole % and about 10.0 mole % of a C2-C9 polycarboxylic acid cross-linking agent, calculated on a cellulose anhydroglucose molar basis, reacted with said fibers in an intrafiber ester crosslink bond form. The C2-C9 polycarboxylic acid cross-linking agent may be selected from the group consisting of:

aliphatic and alicyclic C2-C9 polycarboxylic acids having at least three carboxyl groups per molecule; and aliphatic and alicyclic C2-C9 polycarboxylic acids having two carboxyl groups per molecule and having a carbon-carbon double bond located alpha, beta to one or both of the carboxyl groups, wherein one carboxyl group in said C2-C9 polycarboxylic acid crosslinking agent is separated from a second carboxyl group by either two or three carbon atoms. The fibers may have in particular between about 1.5 mole % and about 6.0 mole % crosslinking agent, calculated on a cellulose anhydroglucose molar basis, reacted therewith in the form of intrafiber ester crosslink bonds. The cross-linking agent may be selected from the group consisting of citric acid, 1, 2, 3, 4 butane tetracarboxylic acid, and 1, 2, 3 propane tricarboxylic acid, in particular citric acid.

Polyacrylic acid cross-linking agents may also be selected from polyacrylic acid homopolymers, copolymers of acrylic acid, and mixtures thereof. The fibers may have between 1.0 weight % and 10.0 weight %, preferably between 3 weight % and 7 weight %, of these cross-linking agents, calculated on a dry fiber weight basis, reacted therewith in the form of intra-fiber crosslink bonds. The cross-linking agent may be a polyacrylic acid polymer having a molecular weight of from 500 to 40,000, preferably from 1,000 to 20,000. The polymeric polyacrylic acid cross-linking agent may be a copolymer of acrylic acid and maleic acid, in particular wherein the weight ratio of acrylic acid to maleic acid is from 10:1 to 1:1, preferably from 5:1 to 1.5:1. An effective amount of citric acid may be further mixed with said polymeric polyacrylic acid cross-linking agent.

The distribution layer comprising cross-linked cellulose fibers of the invention may comprise other fibers, but this layer may advantageously comprise at least 50%, or 60%, or 70%, or 80%, or 90% or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In another example, the layer may comprise about 68% by weight chemically cross-linked cellulose fibers, about 16% by weight untreated pulp fibers, and about 16% by weight PET fibers. In another example, the layer of cross-linked cellulose fibers may comprise from about 90-100% by weight chemically cross-linked cellulose fibers.

The distribution layer 54 may comprise a first zone Z1 towards the front of the article encompassing the point A1 where the distribution layer is of homogenous basis weight, and optionally of homogenous thickness and density, e.g. as seen in FIG. 2. A second zone Z2 may be present towards the back of the article encompassing the point A2 where the distribution layer is of homogenous basis weight, and of optionally homogenous thickness and density. The basis weight of the distribution layer in the second zone Z2 may be at least 20% lower than in the first zone Z1. A transition zone Z3 may be present between Z1 and Z2. As illustrated in FIGS. 1-2, the first zone Z1 and transition zone Z3 may be substantially rectangular as seen in the horizontal plane of the diaper (defined by the longitudinal and transversal axes 80, 90). The second zone Z2 may be also rectangular, or as illustrated in FIGS. 1-2 may have another shape such as a semi-circular shape in the horizontal plane. These shapes are not limiting and any shape for any of the zone is possible, in particular rectangular, square, trapezoidal, circular, conical, semi-circular, ellipsoidal, tapering towards the front or the back of the article or with a tapering as in a "dog bone" or "hour-glass" shape, and combinations thereof. FIGS. 6 and 7 for example show a transition zone Z3 having a trapezoidal shape, as seen in the horizontal plane.

The zone Z2 comprising point A2 may also have a gradually and linearly decreasing basis weight towards the back edge of the article as shown in FIGS. 4 and 5 for example, so that a transition zone is not necessary between the zone Z1 directly surrounding point A1 and the zone Z2 directly surrounding point A2. The zone Z2 in these embodiments may be also semi-circular, for example as shown in FIG. 6 or as represented combined a trapeze and a semi-circular shape as shown in FIG. 8.

The zone Z1 may be larger than Z2. For example, Z1 may have a surface area, as seen from the topside of the article, of at least 50 cm$^2$, or at least 75 cm$^2$ or at least 100 cm$^2$, for example between 100 and 500 cm$^2$. Z2 may have a surface area, as seen from the topside of the article, of at least 10 cm$^2$, or at least 15 cm$^2$ or at least 20 cm$^2$, for example between 20 and 100 cm$^2$. Z3 may have a surface area, as seen from the topside of the article, of at least 10 cm$^2$, or at least 15 cm$^2$ or at least 20 cm$^2$, for example between 20 and 100 cm$^2$.

Although the zones Z1-Z3 have been discussed with reference to the distribution layer, the same proportions for the different zones may apply to the ADS in general and/or to an acquisition layer, if present.

The distribution layer may typically have an average basis weight of from 30 to 400 g/m$^2$, in particular from 100 to 300 g/m$^2$, with the basis weight varying along the length of the article as indicated in the claims. The basis weight in the zone Z1 may for example range from 50 to 400 g/m$^2$, more particularly from 100 to 300 g/m$^2$. The basis weight in the zone Z2 (average basis weight if the zone is not homogeneous) may for example range from 20 to 200 g/m², in particular 30 to 150 g/m². The average basis weight in the transition zone Z3 if present may range for example between 50 and 300 g/m².

Acquisition Layer 52

The ADS may comprise an acquisition layer 52, whose function is to quickly acquire the fluid away from the topsheet so as to provide a good dryness for the wearer. The acquisition layer 52 is typically placed directly under the topsheet. If present, the distribution layer 54 may be at least partially disposed under the acquisition layer 52. The acquisition layer 52 may typically be or comprise a non-woven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round PET staple fibers (50/50 or 40/60 mix of 6 denier and 9 denier fibers). An exemplary binder is a butadiene/styrene latex. Non-wovens have the advantage that they can be manufactured outside the converting line and stored and used as a roll of material.

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and co patent applications US2003/148684 to Cramer et al. and US2005/008839 to Cramer et al.

The acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). In certain embodiments, the binder may be present in the acquisition layer 52 in excess of about 12%, about 14% or about 16% by weight. SB latex is available under the trade name GENFLO™ 3160 (OMNOVA Solutions Inc.; Akron, Ohio).

If present, the acquisition layer 52 may typically have a rectangular shape as seen in the horizontal plane and as shown in the Figures, but it may also have any shapes such as rectangular, square, trapezoidal, circular, conical, semicircular, ellipsoidal, tapering towards the front or the rear of the article or with a central tapering as in a "dog bone" or "hour-glass" shape, and combinations thereof. The acquisition layer may for example comprise a rectangular central part and a rounded end towards the front and/or back of the core in a similar way as shown for the distribution layer 54 e.g. as shown in FIGS. 4, 6 and 8.

A further acquisition layer may be used in addition to a first acquisition layer described above. For example a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13-15 gsm high wet strength made of cellulose fibers from supplier Havix.

Relations Between the Layers

If an acquisition layer is present, it may be advantageous that this acquisition layer is larger than or least as large as the distribution layer in the longitudinal and transversal dimension. Thus the distribution layer can be deposited on the acquisition layer. This simplifies handling, in particular if the acquisition layer is a nonwoven which can be unrolled from a roll of stock material and the distribution layer directly formed by deposition of fibers on the acquisition layer, for example. It is however not excluded that the acquisition layer may be smaller in the plane of the article than the distribution layer. The distribution layer may also be deposited directly on the absorbent core's upper side of the core wrap or another layer of the article.

The absorbent core and in particular its absorbent material deposition area 8 may advantageously be at least as large and long and advantageously at least partially larger and/or longer than the ADS. This is because the SAP layer can usually more effectively retain fluid and provide dryness benefits across a larger area than the ADS. The absorbent article may have a rectangular absorbent material deposition layer and a non-rectangular (shaped) ADS. The absorbent article may also have a rectangular (non-shaped) distribution layer and a rectangular layer of SAP.

Adhesives may be typically used to improve the adhesion of the different layers, for example between the backsheet and the core wrap, typically the glue may be any standard hotmelt glue as known in the art. The glue may be typically sprayed on the whole or part of the surface of one layer before combining the two layers.

Channels

The absorbent material deposition layer in the absorbent core may or may not comprise one or more channels 26,26'. The channels may be relatively large zones within the absorbent material deposition area, which are substantially free of SAP. The channels in the absorbent core may be at least partially oriented in the longitudinal direction of the article and have a length projected on the longitudinal axis which is at least 10% of the length L of the absorbent article, and/or a width W of at least 2 mm at least in some part of the channels. Additional channels may be present, in particular shorter or thinner channels. The ADS may also comprise channels which may or not correspond to the channels in the absorbent core.

The absorbent core may comprise only two channels, for example only in the front region, or for example in the middle (crotch) region and optionally extending into the front and/or back region. The crotch region can be defined as the region of the diaper between point A1 and point A2. The absorbent core may also comprise more than two of such channels, for example at least 4, or at least 5 or at least 6. Some or all of these may be substantially parallel to one another, for example being all straight and completely longitudinally, and/or two or more or all may be mirror images of one another in the longitudinal axis, or two or more may be curved or angled and for example mirror images of one another in the longitudinal axis, and two or more may be differently curved or straight, and for example mirror images of one another in the longitudinal axis. Shorter channels may also be present, for example in the back side or the front side of the core as represented by the pair of channels 27, 27' in FIG. 1.

The channels may be particularly advantageous to help the fluid to penetrate quicker within the absorbent core. The core may comprise one or more channels, in particular one or more pairs of channels symmetrically arranged relative to the longitudinal axis 80. Since the channels may be substantially free of SAP, they will not swell when wet and will be typically clearly visible in wet state, whereas the junction areas which are much smaller and part of the deposition area may not be visible in wet state, as the SAP will expand and may swell into the junction areas.

The channels may be particularly useful when the absorbent material deposition area 8 is rectangular, as the channels can improve the flexibility of the core to an extent that there is less advantage in using a non-rectangular (shaped) core. Of course channels may also be present in a layer of SAP having a shaped deposition area.

The channels may in particular extend substantially longitudinally, which means typically that each channel extends more in the longitudinal direction than in the transverse direction, and typically at least twice as much in the longitudinal direction than in the transverse direction (as measured after projection on the respective axis). There may be no completely or substantially transverse channels in the core.

The channels may be completely oriented longitudinally and parallel to the longitudinal-axis but also may be curved, provided the radius of curvature is typically at least equal (and preferably at least 1.5 or at least 2.0 times this average transverse dimension) to the average transverse dimension of the absorbent layer; and also straight but under an angle of (e.g. from 5°) up to 30°, or for example up to 20°, or up to 10° with a line parallel to the longitudinal axis. This may also includes channels with an angle therein, provided said angle between two parts of a channel is at least 120°, preferably at least 150°; and in any of these cases, provided the longitudinal extension of the channel is more than the transverse extension.

At least one of the channels may have an average width W along its length which is at least 2 mm, or at least 3 mm or at least 4 mm, for example up to 20 mm, or 16 mm. The width of the channel formed by substantially absorbent material and/or SAP free zone in the absorbent material deposition area may be constant through substantially the whole length of the channel or may vary along its length.

The channels are advantageously permanent channels, meaning their integrity is at least partially maintained both in the dry state and in the wet state. Permanent channels may be obtained by provision of one or more adhesive material, for example the fibrous layer of adhesive material or a construction glue that helps adhering for example a substrate with an absorbent material within the walls of the channel. The Wet Channel Integrity Test described below can be used to test if channels are permanent following wet saturation and to what extent.

Permanent channels may be in particular formed by bonding the upper side and lower side of the core wrap (e.g. first substrate 16 and the second substrate 16') together through the channels. Typically, an adhesive can be used to bond both sides of the core wrap through the channels, but it is possible to bond via other known means, for example ultrasonic bonding, or heat bonding. The top side and bottom side of the core wrap can be continuously bonded or intermittently bonded along the channels.

The channels may provide for fast liquid acquisition which reduces risk of leakages. The channels may help to avoid saturation of the absorbent layer in the region of fluid discharge (such saturation increases the risk of leakages). Furthermore, the inventors surprisingly found that, in contrast to what would be expected, whilst the overall amount of SAP material in the absorbent structure is reduced (by providing channels free of such material), the fluid handling properties of the absorbent article are improved. Permanent channels, also have the further advantages that in wet state the superabsorbent polymer cannot move within the core and remains in its intended position, thus providing better fit and fluid absorption.

Advantageously, if present, the channels have a percentage of integrity of at least 20%, or 30%, or 40%, or 50%, or 60, or 70%, or 80%, or 90% following the Wet Channel Integrity Test.

In some embodiments, there is no channel that coincides with the longitudinal axis 80. When present as symmetrical pairs relative to the longitudinal axis, the channels may be spaced apart from one another over their whole longitudinal dimension. The smallest spacing distance may be for example at least 5 mm, or at least 10 mm, or at least 16 mm.

Furthermore, in order to reduce the risk of fluid leakages, the channels may typically not extend up to any of the edges of the absorbent material deposition area 8, and are therefore fully encompassed within this area. Typically, the smallest distance between a channel and the closest edge of the absorbent material deposition area is at least 5 mm.

Fastening System

The diaper 20 may also include a fastening system. The fastening system can be used to provide lateral tensions about the circumference of the diaper 20 to hold the diaper on the wearer. This fastening system is not necessary for training pant article since the waist region of these articles is already bonded. The fastening system usually comprises a fastener such as tape tabs, hook and loop fastening components, interlocking fasteners such as tabs & slots, buckles, buttons, snaps, and/or hermaphroditic fastening components, although any other known fastening means are generally acceptable. A landing zone (not represented) is normally provided on the front waist region for the fastener to be releasably attached. Some exemplary surface fastening systems are disclosed in U.S. Pat. Nos. 3,848,594, 4,662, 875, 4,846,815, 4,894,060, 4,946,527, 5,151,092 and 5,221, 274 issued to Buell. An exemplary interlocking fastening system is disclosed in U.S. Pat. No. 6,432,098. The fastening system may also provide a means for holding the article in a disposal configuration as disclosed in U.S. Pat. No. 4,963, 140 issued to Robertson et al.

The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499, 978, 5,507,736, and 5,591,152.

Front and Back Ears 46, 40

The diaper 20 may comprise front ears 46 and back ears 40 as is known in the art. The ears can be integral part of the chassis, for example formed from the topsheet and/or backsheet as side panel. Alternatively, as represented on FIG. 1, they may be separate elements attached by gluing and/or heat embossing. The back ears 40 are advantageously stretchable to facilitate the attachment of the tabs 42 on the landing zone 40 and maintain the taped diapers in place around the wearer's waist. The back ears 40 may also be elastic or extensible to provide a more comfortable and contouring fit by initially conformably fitting the diaper 20 to the wearer and sustaining this fit throughout the time of wear well past when the diaper 20 has been loaded with exudates since the elasticized ears allow the sides of the diaper 20 to expand and contract.

Leg Cuffs

The diaper 20 may typically comprise leg cuffs which provide improved containment of liquids and other body exudates. Leg cuffs may also be referred to as leg bands, side flaps, barrier cuffs, or elastic cuffs. Usually each leg cuff will comprise one or more elastic string comprised in the chassis of the diaper for example between the topsheet and backsheet in the area of the leg openings to provide an effective seal while the diaper is in use ("gasketing cuffs"). It is also usual for the leg cuffs to comprise "stand-up" elasticized flaps ("barrier leg cuffs") which improve the containment of the leg regions. Each barrier leg cuff typically comprises one or more elastic strings. Typically the barrier leg cuffs are placed further towards the middle of the article than the gasketing cuffs.

U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. describe disposable diapers having "stand-up" elasticized flaps (barrier cuffs) which improve the containment of the leg regions. U.S. Pat. Nos. 4,695,278 and 4,795,454 issued to Lawson and to Dragoo respectively, describe disposable diapers having dual cuffs, including gasketing cuffs and barrier leg cuffs. In some embodiments, it may be desirable to treat all or a portion of the leg cuffs with a lotion, as described above. Leg cuffs are not represented in the Figures for convenience but should be considered present.

Elastic Waist Feature

The diaper 20 may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core 28 and generally forms at least a portion of the end edge of the diaper 20. Disposable diapers can be constructed so as to have two elastic waist features, one positioned in the front waist region and one positioned in the back waist region. The elastic waist feature may be constructed in a number of different configurations including those described in U.S. Pat. Nos. 4,515,595, 4,710,189, 5,151,092 and 5,221,274.

Method of Making the Article

The absorbent article of the invention may be made by any conventional methods known in the art. In particular the articles may be hand-made or industrially produced at high speed. A profiled ADS may be obtained using various techniques. For example if the ADS or part of it is made of a roll of stock material, more layers of the roll of material may be disposed at point A1 than at point A2 to achieve the required dimension of the invention. For example a first layer of ADS may be rolled out and extended from at least A1 to at least A2 and a second layer of the same or different material roll material placed above the first layer from at least A1 but not reaching A2. In this case the basis weight difference at A1 and A2 will be 50%. Two layers may be rolled out between A1 and A2 and a third over A1 but not reaching A2 giving a difference of 33%. If the ADS comprises a fibrous material which is deposited on the converting line, such as cross-linked cellulose it is possible to deposit more of the material in the area surrounding A1 than in the area surrounding A2, as shown for the distribution layer 52 shown in the Figures. Standard equipments used to form profiled core may be used for this purpose. Typically these equipments comprise cavities having the required form connected to a suction device to suck the fibers inside the cavities and form the profiled layer. The formed fibrous layer is then released into a substrate which may itself be a component of the absorbent article, typically a non-woven substrate. Of course it is also possible to make "hand-made" fibrous layers having the required properties.

Experimental Settings

Unless otherwise mentioned, the values indicated herein are measured according to the methods indicated herein below. All measurements are performed at 21±2° C. and 50±20% RH unless specified otherwise.

Centrifuge Retention Capacity (CRC)

The CRC measures the liquid absorbed by the superabsorbent polymer particles for free swelling in excess liquid. The CRC is measured according to EDANA method WSP 241.2-05.

Caliper (Thickness of the Article)

Equipment: Mitutoyo manual caliper gauge with a resolution of 0.01 mm—or equivalent instrument.

Contact Foot: Flat circular foot with a diameter of 20 mm (±0.2 mm). A circular weight may be applied to the foot (e.g., a weight with a slot to facilitate application around the instrument shaft) to achieve the target weight. The total weight of foot and added weight (including shaft) is selected to provide 2.07 kPa (0.30 psi) of pressure to the sample.

The caliper gauge is mounted with the lower surface of the contact foot in a horizontal plane so that the lower surface of the contact foot contacts the center of the flat horizontal upper surface of a base plate approximately 20×25 cm. The gauge is set to read zero with the contact foot resting on the base plate.

Ruler: Calibrated metal ruler graduated in mm.

Stopwatch: Accuracy 1 second

Sample Preparation:

If the absorbent articles are provided in a package, the sample articles to be tested are removed from the center area of a package. If the package contains more than 4 articles, the outer most two articles on each side of the package are not used in the testing. If the package contains more than 4 but fewer than 14 articles, then more than one package of articles is required to complete the testing. If the package contains 14 or more articles, then only one package of articles is required to perform the testing. If the package contains 4 or fewer articles then all articles in the package are measured and multiple packages are required to perform the measurement. Caliper readings should be taken 24±1 hours after the article is removed from the package. Physical manipulation of product should be minimal and restricted only to necessary sample preparation.

Any elastic components of the article that prevent the article from being laid flat under the caliper foot are cut or removed. These may include leg cuffs or waistbands. Pant-type articles are opened or cut along the side seams as necessary. Apply sufficient tension to flatten out any folds/wrinkles. Care is taken to avoid touching and/or compressing the absorbent core and ADS area. The length of the article is measured along the longitudinal centerline of the article from the front edge to the back edge.

Measurement Procedure:

The article is laid flat on a counter top, garment-facing side down. A lateral line is drawn across the body-facing surface of the article at a defined distance D from the diaper front and back edge. The distance D is defined as 32% of the total length of the article. The intersections between the lateral lines at distance D with the longitudinal centerline are marked using a permanent felt tip marker. These intersections represent the locations where the center of the caliper foot is placed during the caliper measurement and are referred to the "back caliper" and "front caliper" measurement points.

The contact foot of the caliper gauge is raised and the article is placed on base plate, garment-facing surface side down so that when lowered, the center of the foot is on one of the marked measuring points.

The foot is gently lowered onto the article and released (ensure calibration to "0" prior to the start of the measurement). The caliper value is read to the nearest 0.01 mm, 10 seconds after the foot is released.

The procedure is repeated for each measuring point. If there is a fold at the measuring point, the measurement is done in the closest area to this point but without any folds.

Ten articles are measured in this manner for a given product and the "average front caliper" and the "average back caliper" value is calculated and reported with an accuracy of one tenth mm.

Basis Weight of the Ads or its Component Layers

The basis weight of the ADS, or any of its component layers such as acquisition layer and distribution layer, at the points A1 and A2 will typically be known by the manufacturer from the product making specification. However, if the basis weight is not known for a given article, the basis weight can be measured in the following manner. The measurements should be made on 10 similar articles and the values measured averaged.

The basis weight is measured by die-cutting a circular sample of the absorbent article having a 1 cm diameter centered on the point A1 and A2 respectively. If the points A1 and/or A2 are on the edge of the ADS so that it not possible to die cut the ADS exactly centering on the points A1 or A2, the die cutting tool is slightly moved (by a maximum of 5 mm) towards the center of the article so that the edge of the die cut coincides with the edge of the ADS.

The material of the ADS or its component layers in the sample is then separated from the materials of the other layers. The material of interest is weighed on an accurate scale (within ±0.0001 g), the weight and area of the sample determining the basis weight.

Wet Channel Integrity Test

This test is designed to check the integrity of a channel in an absorbent core following wet saturation.

1. The full length (in millimeters) of the channel is measured in the dry state (if the channel is not straight, the curvilinear length through the middle of the channel is measured).

2. The absorbent core is then completely immersed in a large excess (e.g. 5 liters) of synthetic urine "Saline", with a concentration of 9.00 g NaCl per 1000 ml solution prepared by dissolving the appropriate amount of sodium chloride in distilled water. The temperature of the solution must be 20+/−5° C.

3. After 1 minute in the saline, the core is removed and held vertically by one end for 5 seconds to drain, then extended flat on an horizontal surface with the top side (the side intended to be facing the wearer in the article) facing up. If the core comprises stretch elements, it is pulled taut so that no contraction is observed. The core can be fixed to an horizontal surface by clamps at its front edge and back edge, so that no contraction can happen.

4. The absorbent core is covered with a rectangular suitably weighted rigid plate, with dimensions as follows: length equal to the full length of the core, and width equal to the maximum core width at the widest point.

5. A pressure of 18.0 kPa is applied for 30 seconds over the area of the rigid plate above mentioned. Pressure is calculated on the basis of overall area encompassed by the rigid plate. Pressure is achieved by placing additional weights in the geometric center of the rigid plate, such that the combined weight of the rigid plate and the additional weights result in a pressure of 18.0 kPa over the total area of the rigid plate.

6. After 30 seconds, the additional weights and the rigid plate are removed.

7. Immediately afterwards, the cumulative length of the portions of the channel which remained intact is measured (in millimeters; if the channel is not straight, the curvilinear length through the middle of the channel is measured). If no portions of the channel remained intact then the channel is not permanent.

8. The percentage of integrity of the permanent channel is calculated by dividing the cumulative length of the portions of the channel which remained intact by the length of the channel in the dry state, and then multiplying the quotient by 100.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a front end, a back end and a longitudinal axis extending in a longitudinal direction of the article, the article having a length L as measured along the longitudinal axis between the front end and the back end, the absorbent article comprising:
   a liquid permeable topsheet;
   a liquid impermeable backsheet;
   an absorbent core comprising a core wrap enclosing an absorbent material; and an acquisition-distribution system at least partially disposed between the absorbent core and the topsheet and comprising two or more layers; wherein the acquisition-distribution system extends in the longitudinal direction of the absorbent article at least from a point A1 disposed at a distance D from the front end to a point A2 disposed at the distance D from the back end of the article, wherein the distance D is equal to about 32% of the length L of the article, wherein the acquisition-distribution system has a basis weight which is lower at the point A2 than at the point A1 and wherein the acquisition-distribution system comprises an acquisition layer and a distribution layer and does not comprise superabsorbent polymer, wherein the acquisition layer is disposed closer to the topsheet than the distribution layer and the distribution layer is profiled along the longitudinal axis such that the basis weight of the distribution layer at the point A2 is at least about 20% lower than at the point A1, and wherein the acquisition-distribution system comprises a first zone Z1 disposed towards the front end and encompassing point AL, and a second zone Z2 disposed towards the back end and encompassing point A2;

wherein the first zone Z1 comprises a homogenous basis weight and the second zone Z2 comprises a gradually, linearly decreasing basis weight.

2. The absorbent article of claim 1, wherein the caliper of the absorbent article at the point A2 is at least about 20% lower than the caliper of the absorbent article at the point A1, as measured according to the Caliper Test as disclosed by the instant specification.

3. The absorbent article of claim 1, wherein the first zone Z1 comprises a larger surface area than the second zone Z2.

4. The absorbent article of claim 1, wherein the acquisition layer comprises a latex-bonded nonwoven.

5. The absorbent article of claim 1, wherein the periphery of the area of the absorbent material within the core wrap defines an absorbent material deposition area, and wherein the acquisition-distribution system does not extend beyond any edges of the absorbent material deposition area.

6. The absorbent article of claim 1, wherein the absorbent material of the absorbent core comprises at least 80% of superabsorbent polymers by total weight of the absorbent material.

7. The absorbent article of claim 1, wherein the absorbent material of the absorbent core comprises less than 10% of natural or synthetic fibers by total weight of the absorbent material.

8. The absorbent article of claim 1, wherein the absorbent core comprises at least one channel substantially free of superabsorbent polymers.

* * * * *